United States Patent [19]

Devore et al.

[11] Patent Number: 5,425,872
[45] Date of Patent: Jun. 20, 1995

[54] ELECTROCHEMICAL PREPARATION OF ADDITION POLYMERIZATION CATALYSTS

[75] Inventors: David D. Devore; Robert D. Mussell; James C. Stevens; Francis J. Timmers, all of Midland, Mich.

[73] Assignee: The Dow Chemical Company

[21] Appl. No.: 275,579

[22] Filed: Jul. 15, 1994

Related U.S. Application Data

[62] Division of Ser. No. 82,201, Jun. 24, 1993, Pat. No. 5,372,682.

[51] Int. Cl.$^6$ ................................................. C25B 3/12
[52] U.S. Cl. ................................ 204/59 QM; 204/72; 204/81

[58] Field of Search .................... 204/72, 81; 526/126, 526/134, 160, 170; 556/11, 17, 19, 22, 53, 54, 56

[56] References Cited

U.S. PATENT DOCUMENTS 5,064,802  11/1991  Stevens et al. ................ 502/155
5,189,192  2/1993  LaPointe et al. ................ 556/11

OTHER PUBLICATIONS

Inorg. Chem., 31, 5345–5346 (May 1992).

*Primary Examiner*—John Niebling
*Assistant Examiner*—Edna Wong

[57] ABSTRACT

Group 4 metal complexes useful as addition polymerization catalysts are prepared by electrolysis of cyclopentadienyl metal complexes under inert electrolysis conditions.

21 Claims, No Drawings

ELECTROCHEMICAL PREPARATION OF ADDITION POLYMERIZATION CATALYSTS

This application is a divisional of copending application Ser. No. 08/082,201, filed Jun. 24, 1993, now U.S. Pat. No. 5,372,682.

BACKGROUND OF THE INVENTION

This invention relates to a process for preparing certain catalytically active metal complexes. More particularly, this invention relates to such a process involving electrochemical means for conversion of a complex to an active catalytic form useful for polymerizing olefins, diolefins and/or acetylenically unsaturated monomers.

In U.S. Pat Nos. 5,064,802 and 5,132,380, cationic Group 4 metal catalysts having unique activity as addition polymerization catalysts are disclosed and claimed. In U.S. Pat No. 5,189,192, a process for single step metal center oxidation and cation complex formation of such metal complexes is disclosed. In pending U.S. application U.S. Ser. No. 547,718, filed Jul. 3, 1990, there is disclosed a molecular oxidative activation procedure for preparing the same or similar complexes. For the disclosures contained therein the preceding pending application and issued patents are hereby incorporated by reference in their entireties.

In the above oxidation processes, a chemical oxidizing agent is employed to convert the initial metal complex to the active catalytic species. Such chemical oxidizing agents result in the generation of byproducts that may be environmentally unacceptable and are desirably removed from the resulting catalyst product. Such removal step complicates the preparation method.

In *Inorg. Chem.*, 31, 5345–5346 (1992), the one-electron electrochemical oxidation of biscyclopentadienyltitanium dichloride in acetonitrile solvent using tetrabutylammonium tetrafluoroborate supporting electrolyte is disclosed. The tetrafluoroborate counter ion is a coordinating ligand and the acetonitrile solvent is both reactive and coordinating under the conditions of the electrolysis. Accordingly, the resulting cationic product, biscyclopentadienyltitanium chloro acetonitrile tetrafluoroborate ($Cp_2TiCl(CH_3CN)+BF_4^-$) is not catalytically active for addition polymerizations.

The present invention lies in the discovery of a novel electrochemical technique for preparing certain catalytically active Group 4 metal complexes. By electrochemical activation, an improved and greatly simplified method of catalyst preparation is provided. Moreover, the present process does not result in formation of byproducts from chemical oxidants that contaminate the desired catalyst. Further, due to the absence of coordinating or reactive species in the reaction, a highly active addition polymerization catalyst is produced. Finally, since the electrolysis may be monitored to achieve precise conversion of only the desired materials, no excess oxidant is left in the resulting product. Thus, a highly efficient method for preparing the desired metal complexes is provided.

SUMMARY OF THE INVENTION

In accordance with the present invention there is provided a process for the preparation of metal complexes corresponding to the formula:

$$Cp_aZ_bM(IV)X_c^+ A^- \qquad (1)$$

wherein:
- Cp independently each occurrence is a cyclopentadienyl group $\pi$-bound to M; a hydrocarbyl, silyl, germyl, halo, cyano, or halohydrocarbyl substituted derivative of said cyclopentadienyl group; or such a substituted cyclopentadienyl group wherein two such substituents (other than halo or cyano) together form a multiple ring structure, said Cp containing up to 50 nonhydrogen atoms, and when more than one Cp is present, different Cp moieties may be joined by a linking group;
- Z is a divalent moiety bound to both Cp and M(IV) comprising boron, or a member of Group 14 of the Periodic Table of the Elements, and optionally nitrogen, phosphorus, sulfur or oxygen, said moiety having up to 30 non-hydrogen atoms, and optionally Cp and Z together form a fused ring system;
- M(IV) is a Group 4 metal in the +4 oxidation state;
- X independently each occurrence is hydride; halide; or a covalently bonded ligand group selected from hydrocarbyl, silyl, germyl, and combinations thereof, said X having up to 50 carbon, silicon or germanium atoms, and oxygen, nitrogen, phosphorus or sulfur containing derivatives thereof;
- a is 1 or 2;
- if a is 1, b is 0 or 1, if a is 2, b is 0;
- c is 1 or 2;
- the sum of a+b+c equals 3; and
- $A^-$ is an inert, compatible, noncoordinating anion, the steps of the process comprising electrolyzing under inert electrolysis conditions at least one initial complex corresponding to the formula:

$$Cp_aZ_bM(III)X_c \text{ or} \qquad (1a)$$

$$Cp_aZ_bM(IV)X_{c+1}, \qquad (1b)$$

to produce complexes of formula (1); wherein:
M(III) is a Group 4 metal in the +3 oxidation state, and Cp, Z, M(IV), X, a, b, and c, are as previously defined.

The activated metal complexes resulting from the electrolysis (including mixtures of the reaction products) have been found to be highly active addition polymerization catalysts. Consequently, there is also provided according to the present invention an addition polymerization catalyst comprising the reaction product resulting from electrolyzing under inert, noncoordinating, electrolysis conditions at least one initial complex corresponding to the formula:

$$Cp_aZ_bM(III)X_c \text{ or} \qquad (1a)$$

$$Cp_aZ_bM(IV)X_{c+1}; \qquad (1b)$$

wherein M(III), M(IV), Cp, Z, X, a, b, and c, are as previously defined.

In a final embodiment there is provided a polymerization process comprising contacting one or more addition polymerizable monomers with the above reaction product under addition polymerization conditions to prepare a polymer and recovering the polymer.

DETAILED DESCRIPTION

All reference to the Periodic Table of the Elements herein shall refer to the Periodic Table of the Elements, published and copyrighted by CRC Press, Inc., 1989.

Also, any reference to a Group or Groups shall be to the Group or Groups as reflected in this Periodic Table of the Elements using the IUPAC system for numbering groups.

As used herein, the recitation "compatible noncoordinating anion" means an anion which when functioning as a charge balancing anion in the catalyst system of this invention does not transfer an anionic substituent or fragment thereof to any cationic species thereby forming a neutral metal product. "Compatible anions" are anions which are not degraded to neutrality during catalyst preparation or use.

In a preferred embodiment $A^-$ comprises an anion which is a single coordination complex comprising a plurality of lipophilic radicals covalently coordinated to and shielding a central, formally negative chargebearing atom, which anion is stable under the oxidation and subsequent polymerization conditions, and which anion is compatible with and noncoordinating towards the resulting Group 4 metal containing catalyst. The anion is employed only to provide charge balance without interfering with the electrolysis or the catalytic properties of the resulting catalyst. Any Group 13 atom capable of forming a coordination complex which is stable under the reaction conditions of the present invention may be contained in the anion.

Particularly preferred Group 13 atom containing anions are boron compounds represented by the following general formula:

$$[BQ_4]^-$$

wherein Q independently each occurrence is a nonreactive, covalently bonded organyl or silyl radical containing from 6 to 20 carbon or silicon atoms. In addition two or more Q groups may be linked to each other through a stable bridging group. Preferably, Q lacks reactive hydrogen moieties. That is, the radicals are either devoid of hydrogen, contain only hydrogen in nonactivated positions or contain sufficient steric hindrance to protect potentially active hydrogen sites. Examples of preferred Q radicals are perfluorinated hydrocarbyl radicals containing from 1 to 20 carbon atoms, 3,4,5-trifluorophenyl, and 3,5-di(trifluoromethyl)phenyl. Also, one Q group may be a $C_{1-10}$ organyl group, especially methyl or benzyl, without detrimentally affecting the inert properties of the anion. A most highly preferred inert, compatible, non-coordinating, anion is tetrakis(-pentafluorophenyl)borate.

Preferred substituents of the Cp group(s) are hydrocarbyl or halosubstituted hydrocarbyl groups, said groups having from 1 to 30 carbons, or divalent derivatives of 2 such hydrocarbyl or halosubstituted hydrocarbyl groups which together cause Cp to possess a fused ring structure.

Exemplary hydrocarbyl radicals include straight, branched, or cyclic alkyl or alkenyl radicals, aryl substituted alkyl radicals, and fused or covalently bonded aryl radicals and alkyl-substituted aryl radicals. Preferred are methyl, ethyl, butyl and phenyl radicals. Exemplary silyl or germyl radicals include trimethylsilyl, triethylsilyl, ethyldimethylsilyl, methyldiethylsilyl, dimethyl-t-butylsilyl, triphenylsilyl, triphenylgermyl, and trimethylgermyl radicals.

More particularly, suitable cyclopentadienylor substituted cyclopentadienyl- groups in the present complexes where b is 0, are illustrated by formula (I):

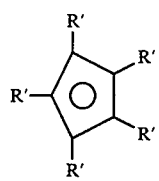

wherein:
wherein R' each occurrence is independently selected from the group consisting of hydrogen, alkyl, aryl, silyl, germyl, cyano, halo and combinations thereof, said R' having up to 20 non-hydrogen atoms, or two R' groups (when R' is not hydrogen, cyano or halo) together form a divalent derivative thereof connected to adjacent positions of the cyclopentadienyl ring.

Preferably, R' independently each occurrence is hydrogen, methyl, ethyl, propyl, butyl, pentyl, hexyl, (including where appropriate all isomers), cyclopentyl, cyclohexyl, norbornyl, benzyl, or phenyl or adjacent R' groups are linked together thereby forming an indenyl, tetrahydroindenyl, fluorenyl, tetrahydrofluorenyl, or octahydrofluorenyl group.

One embodiment of the invention relates to biscyclopentadienyl compounds including those containing a bridging group linking the cyclopentadienyl groups. Preferred bridging groups are those corresponding to the formula $(JR''_2)_x$ wherein J is silicon or carbon, R'', independently each occurrence is hydrogen or a group selected from silyl, hydrocarbyl and combinations thereof, said R'' having up to 30 carbon or silicon atoms, and x is 1 to 8, more preferably x is 1 or 2. Preferably R'' independently each occurrence is methyl, benzyl, tert-butyl, or phenyl.

Examples of the foregoing bridged cyclopentadienyl group containing complexes are compounds corresponding to formula (II):

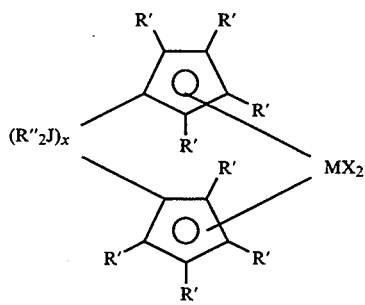

wherein:
J, R', R'' and x are as previously defined.

Such bridged structures are especially suited for the preparation of polymers having stereoregular molecular structure. In such capacity it is preferred that the complex possess a chiral, stereorigid structure. Examples of this type are compounds possessing different delocalized $\pi$-bonded systems, such as one cyclopentadienyl group and one indenyl group.

When the ligand moiety consisting of —Cp—Z—, is present, it is dianionic, having the ionic charges residing formally on Cp and Z.

Preferably M(III) and M(IV) are titanium.

X preferably includes chloride, primary, secondary or tertiary alkyl, aryl, aralkyl; cycloalkyl, alkoxide; dialkylaminoalkyl; dialkylaminoaryl, dialkylaminoaralkyl; allyl; dialkylphosphinoalkyl; and dialkylphosphinoaralkyl. It has been found highly desirable for complexes comprising M(III), that X be capable of stabilizing the resulting complex. In such case X preferably is allyl, $C_{1-10}$ hydrocarbyl substituted allyl, —NR'''$_2$, —PR'''$_2$ or —OR''' substituted $C_{1-10}$ hydrocarbyl, wherein R''' is $C_{1-10}$ hydrocarbyl. Especially desirable X groups are allyl, 2-N,N-dimethylaminophenyl or 2-N,N-dimethylaminobenzyl.

Preferred complexes prepared according to the present invention are monocyclopentadienyl titanium compounds corresponding to formula (III):

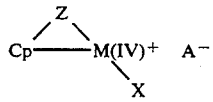

III wherein:
Z, M(IV), X, and A— are as previously defined; and
Cp is a cyclopentadienyl group bound to Z and bound in an $\eta^5$ bonding mode to M(IV) or such an $\eta^5$ bonded cyclopentadienyl group substituted with from one to four substituents independently each occurrence selected from the group consisting of hydrocarbyl, silyl, germyl, halo, and mixtures thereof, said substituent having up to 20 nonhydrogen atoms, or optionally, two substituents (except halo) together cause Cp to have a fused ring structure. Highly preferred metal complexes prepared according to the present invention are compounds corresponding to formula (IV):

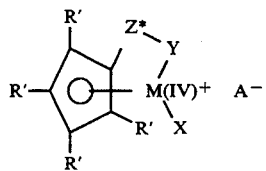

IV wherein:
M(IV), R' and A$^-$ are as previously defined;
Y is an anionic ligand group comprising nitrogen, phosphorus, oxygen or sulfur and having up to 20 non-hydrogen atoms, said Y being bonded to Z* and M through a chain comprising said nitrogen, phosphorus, oxygen or sulfur, and optionally Y and Z* together form a fused ring system;
Z* is SiR*$_2$, CR*$_2$, SiR*$_2$SiR*$_2$, CR*$_2$CR*$_2$, CR*=CR*, CR*$_2$SiR*$_2$, GeR*$_2$;
R* each occurrence is independently selected from the group consisting of hydrogen, alkyl, aryl, silyl, halogenated alkyl, halogenated aryl groups, said R* having up to 20 non-hydrogen atoms, and mixtures thereof, or two R* groups from Z*, or an R* group from Z* together with Y forms a fused ring system; and
X independently each occurrence is hydride, halo, alkyl, aryl, aralkyl, allyl, hydrocarbyl substituted allyl, dialkylaminoaryl, dialkylaminoaralkyl, aryloxy or alkoxy, said X having up to 20 carbons.

Most preferably, Y is —O—, —S—, —NR*— or —PR*—. Highly preferably Y is a nitrogen or phosphorus containing group corresponding to the formula —N(R'''')—or —P(R'''')—, wherein R'''' is $C_{1-10}$ alkyl.

Most highly preferred metal coordination complexes correspond to formula (V):

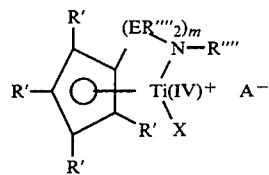

V wherein:
R' each occurrence is independently selected from the group consisting of hydrogen, silyl, alkyl, aryl and combinations thereof, said R' having up to 10 carbon or silicon atoms, or two R' groups (when R' is not hydrogen) together form a divalent derivative thereof;
R'''' is as previously defined;
E is silicon or carbon;
X is alkyl, aryl, allyl or dialkylaminoaralkyl, said X having up to 20 carbons; and
m is 1 or 2.

The term "inert electrolysis conditions" as used herein refers to the use of solvents, supporting electrolytes and electrolytic potentials for the electrolysis such that electrolysis byproducts that would render the metal complex catalytically inactive are not formed during the reaction. More particularly, suitable solvents are materials that are: liquids under the conditions of the electrolysis (generally temperatures from 0° to 100° C.), capable of dissolving the supporting electrolyte, and inert. "Inert solvents" are those that are not reduced or oxidized under the reaction conditions employed for the electrolysis. It is generally possible in view of the desired electrolysis reaction to choose a solvent and a supporting electrolyte that are unaffected by the electrical potential used for the desired electrolysis. Examples of preferred solvents include difluorobenzene (all isomers), and $C_{1-6}$ dialkyl ethers of(poly)alkylene glycols, especially dimethoxyethane, and mixtures of the foregoing. Generally, solvents that are Lewis bases, especially nitrile, ether, amine, and phosphine compounds may be used, however such solvents may coordinate with the metal complex. Accordingly, these solvents should be removed from the resulting catalyst mixtures prior to use. Suitably, devolatilization under reduced pressure or other evaporative techniques may be used to purify the desired catalyst.

The electrolysis may be conducted in a standard electrolytic cell containing an anode and cathode (also referred to as the working electrode and counter electrode, respectively). Suitable materials of construction for the cell include glass, plastic, ceramic, glass coated metal, etc. The electrodes are prepared from inert conductive materials, by which are meant conductive materials that are unaffected by the reaction mixture or reaction conditions. Platinum or palladium are preferred inert conductive materials. Normally an ion permeable membrane such as a fine glass frit separates the cell into separate compartments, the working electrode compartment and counter electrode compartment. A third, buffering or spacer, compartment may separate the working electrode compartment and counter electrode compartment. The working electrode is immersed in a reaction medium comprising the metal complex to be activated, solvent, supporting electrolyte, and any other materials desired for moderating the electrolysis or stabilizing the resulting complex. The counter electrode is immersed in a mixture of the solvent and an electrolyte comprising the A$^-$ anion, which electrolyte may also be the supporting electrolyte. The desired voltage may be determined by theoretical calculations or determined experimentally by sweeping the cell using a reference electrode such as a silver electrode immersed in the cell electrolyte. The background cell current, the current draw in the absence of the desired electrolysis, is also determined. The electrolysis is completed when the current drops from the desired level to the background level. In this manner, complete conversion of the initial metal complex can be easily detected.

Suitable supporting electrolytes are salts corresponding to the formula $G^+A^-$; wherein:

$G^+$ is a cation which is nonreactive towards the starting and resulting complex, and $A^-$ is as previously defined.

Examples of cations, $G^+$, include $C_{4-40}$ tetrahydrocarbyl substituted ammonium or phosphonium cations having up to 30 nonhydrogen atoms. A preferred cation is the tetra-n-butylammonium cation.

During the practice of the invention the cation of the supporting electrolyte passes to the counter electrode and $A^-$ migrates to the working electrode to become the anion of the resulting oxidized product. Either the solvent or the cation of the supporting electrolyte is reduced at the counter electrode in equal molar quantity with the amount of oxidized metal complex formed at the working electrode. Preferred supporting electrolytes in this embodiment of the invention are $C_{4-14}$ tetraalkylammonium salts of tetrakisperfluoroaryl borates, especially tetra-n-butylammonium tetrakispentafluorophenyl borate.

The complexes resulting from the present process may be used as catalysts to polymerize ethylenically and/or acetylenically unsaturated monomers having from 2 to 50 carbon atoms either alone or in combination. Preferred monomers are $C_{2-20}$ α-olefins and mixtures thereof. In general, the polymerization may be accomplished at conditions well known in the prior art for Ziegler-Natta or Kaminsky-Sinn type polymerization reactions, ie. temperatures from 0°–250° C. and pressures from atmospheric to 1000 atmospheres. Suspension, solution, slurry, gas-phase or other process condition may be employed if desired. A support may be employed if desired, also a weakly coordinating or otherwise stabilizing Lewis base compound such as a bulky olefin that is incapable of polymerization when contacted with the catalyst may be added to the complex.

Optionally a secondary component selected from the group consisting of polymeric or oligomeric aluminoxanes, especially methylalumoxane or isobutylalumoxane, and $C_{3-30}$ trialkylaluminum compounds, especially triethylaluminum or triisobutylaluminum may be added to the reaction mixture resulting from the electrolysis. The presence of the secondary component in the mixture when the same is used as an addition polymerization catalyst, particular for the polymerization of α-olefins such as ethylene, results in improved catalyst efficiency.

Suitable solvents for the solution polymerization are noncoordinating, inert liquids. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and the like and aromatic and alkyl-substituted aromatic compounds such as benzene, toluene, xylene and the like. Suitable solvents also include liquid olefins which may act as monomers or comonomers including ethylene, propylene, butadiene, cyclopentene, 1-hexane, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable.

The complex formed by the method of this invention may be retained in solution or separated from the solvent and supporting electrolyte and stored for subsequent use. Preferably, if it is separated from the electrolysis solvent and supporting electrolyte, the complex is extracted in a hydrocarbon solvent, such as toluene or a mixed alkane, and concentrated or recrystallized if desired. In most polymerizations the molar ratio of catalyst:polymerizable compound employed is from $10^{-12}$:1 to $10^{-1}$: 1, more preferably from $10^{-12}$:1 to $10_{-5}$:1.

Having described the invention the following examples are provided as further illustration thereof and are not to be construed as limiting. Unless stated to the contrary all parts and percentages are expressed on a weight basis.

EXAMPLES 1–4

Complex Preparation

A standard H-cell for electrolysis comprising two electrode wells separated by a fine glass frit, platinum mesh working and counter electrodes, and a silver reference electrode was placed inside an inert atmosphere glove box filled with argon. Each half of the cell was filled with 1,2-difluorobenzene solvent (5 ml in the working compartment, 4 ml in the counter compartment in each compartment) and tetra-n-butylammonium tetrakisperfluorophenylborate supporting electrolyte (6 mmole in each compartment). The complex to be oxidized was placed in the working compartment. A sweep of the working electrode potential was used to determine the voltage to be applied during electrolysis. The solution was stirred and the potential was stepped to the appropriate value to start electrolysis. The applied potential was turned off when it dropped to the background level. The working compartment solution was then pipetted into a round bottom flask and the solvent was removed under vacuum. The product was dissolved in toluene and a quantity sent to a polymerization reactor. Further details of the initial complex and electrolysis conditions used in the preparation are contained in Table I.

TABLE I

| Run | initial complex | amount (g) | potential (V)* | final complex |
|---|---|---|---|---|
| 1 | $(C_5Me_4SiMe_2NBu)Ti(III)(O—CH_2C_6H_4NMe_2)$ | 0.017 | −1.0 | A |
| 2 | $(C_5Me_4SiMe_2NBu)Ti(IV)(CH_3)_2$ | 0.013 | +1.4 | B |
| 3 | $(C_5Me_4SiMe_2NBu)Ti(IV)(Cl)_2$ | 0.015 | +2.2 | C |
| 4 | $(C_5Me_4SiMe_2NBu)Ti(IV)(CH_2C_6H_5)_2$ | 0.019 | +1.0 | D |

*potential relative to ferrocene reduction half-cell

TABLE I-continued (A) [Structure: Me4C5-SiMe2-N-C(CH3)3, Ti(IV)+ with CH3 and o-CH2C6H4N(CH3)2 ligands] [B(C6F5)4]−

(B) [Structure: Me4C5-SiMe2-N-C(CH3)3, Ti(IV)+ with CH3 and CH3 ligands] [B(C6F5)4]−

(C) [Structure: Me4C5-SiMe2-N-C(CH3)3, Ti(IV)+ with CH3 and Cl ligands] [B(C6F5)4]−

(D) [Structure: Me4C5-SiMe2-N-C(CH3)3, Ti(IV)+ with CH3 and CH2C6H5 ligands] [B(C6F5)4]−

Polymerizations

A 2 L stirred reactor was charged with the desired amounts of mixed alkane solvent (Isopar ™ E, available from Exxon Inc.) and 1-octene comonomer. The reactor was heated to 140° C. and saturated with ethylene at 500 psig (3.5 MPa). Hydrogen chain terminator was added by differential pressure expansion from a ~75 mL addition tank to provide the indicated hydrogen pressure differential. Catalysts were prepared in an inert atmosphere drybox by electrolysis as indicated above. The desired amount of metal complex solution (in toluene), optionally containing a secondary component (triisobutyl aluminum) was added via syringe to a catalyst addition tank for injection into the reactor. The polymerization was allowed to proceed for the indicated run time and the solution was removed from the reactor and quenched with hindered phenol anti-oxidant and precipitated with isopropanol. The polymers were air-dried overnight and then dried in a vacuum oven.

Results are contained in Table II.

TABLE II

| Polym. Run | Catalyst | Cat. Amt. (μmole) | Co-catalyst | Cocatalyst (μmol) | Solvent (g) | 1-octene (g) | $\Delta H_2$ (kPa) | time (min) | Polymer (g) | efficiency (g/g metal) |
|---|---|---|---|---|---|---|---|---|---|---|
| 1 | A[1] | 2.0 | — | — | 741 | 122 | 180 | 15 | 60.1 | 627,000 |
| 2 | B[2] | 1.0 | — | — | 744 | 108 | 170 | " | 46.8 | 977,000 |
| 3 | C[3] | 5.0 | TIBA[5] | 200 | 744 | 108 | 280 | 10 | 9.5 | 40,000 |
| 4 | D[4] | 2.0 | — | — | 744 | 122 | 170 | 15 | 45.5 | 474,000 |

[1] [(Me4C5SiMe2N-tert-Bu)Ti(III)(o-CH2C6H4NMe2)]+ [(C6F5)4B]−
[2] [(Me4C5SiMe2N-tert-Bu)Ti(IV)CH3]+ [(C6F5)4B]−
[3] [(Me4C5SiMe2N-tert-Bu)Ti(IV)Cl]+ [(C6F5)4B]−
[4] [(Me4C5SiMe2N-tert-Bu)Ti(IV)CH2C6H5]+ [(C6F5)4B]−
[5] triisobutyl aluminum

What is claimed is:

1. A process for the preparation of metal complexes corresponding to the formula:

$$Cp_a Z_b M(IV) X_c^+ A^-, \quad (1)$$

wherein:

Cp independently each occurrence is a cyclopentadienyl group π-bound to M; a hydrocarbyl, silyl, germyl, halo, cyano, or halohydrocarbyl substituted derivative of said cyclopentadienyl group; or such a substituted cyclopentadienyl group wherein two such substituents together form a multiple ring structure, said Cp containing up to 50 nonhydrogen atoms, and when more than one Cp is present, different Cp moieties may be joined by a linking group;

Z is a divalent moiety bound to both Cp and M(IV) comprising boron, or a member of Group 14 of the Periodic Table of the Elements, and optionally nitrogen, phosphorus, sulfur or oxygen, said moiety having up to 30 non-hydrogen atoms, and optionally Cp and Z together form a fused ring system;

M(IV) is a Group 4 metal in the +4 oxidation state;
X independently each occurrence is hydride; halide; or a covalently bonded ligand group selected from hydrocarbyl, silyl, germyl, and combinations thereof, said X having up to 50 carbon, silicon or germanium atoms, and oxygen, nitrogen, phosphorus or sulfur containing derivatives thereof;
a is 1 or 2;
if a is 1, b is 0 or 1, if a is 2, b is 0;
c is 1 or 2;
the sum of a+b+c equals 3; and
$A^-$ is an inert, compatible, noncoordinating anion, the steps of the process comprising electrolyzing under inert, noncoordinating, electrolysis conditions at least one initial complex corresponding to the formula:

$$Cp_a Z_b M(III) X_c \text{ or} \quad (1a)$$

$$Cp_a Z_b M(IV) X_{c+1}, \quad (1b)$$

in the presence of an electrolyte comprising $A^-$ to produce complexes of formula (1); wherein:

M(III) is a Group 4 metal in the +3 oxidation state; and Cp, Z, M(IV), X, a, b, and c, are as previously defined above.

2. A process according to claim 1, wherein $A^-$ is tetrakispentafluorophenylborate.

3. A process according to claim 1, wherein M is titanium.

4. A process according to claim 1, wherein the complex formed corresponds to the formula:

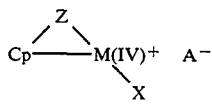

wherein:
Z, M(IV), X, and A⁻ are as previously defined in claim 1;
Cp is a cyclopentadienyl group bound to Z and bound in an $\eta^5$ bonding mode to M(IV) or such an $\eta^5$ bonded cyclopentadienyl group substituted with from one to four substituents independently each occurrence selected from the group consisting of hydrocarbyl, silyl, germyl, halo, and mixtures thereof, said substituent having up to 20 non-hydrogen atoms, or optionally, two substituents together cause Cp to have a fused ring structure.

5. A process according to claim 4 wherein A⁻ is tetrakispentafluorophenylborate.

6. A process according to claim 4 wherein M is titanium.

7. A process according to claim 4 wherein the complex formed corresponds to the formula:

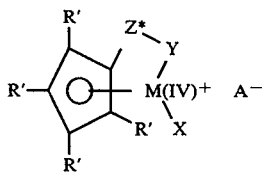

wherein:
M(IV) and A⁻ are as previously defined;
R' each occurrence is independently selected from the group consisting of hydrogen, alkyl, aryl, silyl, germyl, halo and combinations thereof, said R' having up to 30 non-hydrogen atoms, or two R' groups together form a divalent derivative of such groups;
Y is an anionic ligand group comprising nitrogen, phosphorus, oxygen or sulfur and having up to 20 non-hydrogen atoms, said Y being bonded to Z* and M through a chain comprising said nitrogen, phosphorus, oxygen or sulfur, and optionally Y and Z* together form a fused ring system;
Z* is SIR*₂, CR*₂, SiR*₂SiR*₂, CR*₂CR*₂, CR*=CR*, CR*₂SiR*₂, GeR*₂; wherein:
R* each occurrence is independently selected from the group consisting of hydrogen, alkyl, aryl, silyl, halogenated alkyl, halogenated aryl groups, said R* having up to 20 non-hydrogen atoms, and mixtures thereof, or two R* groups from Z*, or an R* group from Z* together with Y forms a fused ring system; and
X independently each occurrence is hydride, halo, alkyl, aryl, aralkyl, allyl, hydrocarbyl substituted allyl, dialkylaminoaryl, dialkylaminoaralkyl, aryloxy or alkoxy, said X having up to 20 carbons.

8. A process according to claim 7 wherein A⁻ is tetrakispentafluorophenylborate.

9. A process according to claim 7 wherein M is titanium.

10. A process according to claim 7 wherein the complex formed corresponds to the formula:

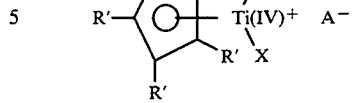

wherein:
R' each occurrence is independently selected from the group consisting of hydrogen, silyl, alkyl, aryl and combinations thereof, said R' having up to 10 carbon or silicon atoms, or two R' groups together form a divalent derivative thereof;
R'''' is $C_{1-10}$ hydrocarbyl;
E is silicon or carbon;
X is alkyl, aryl, allyl or dialkylaminoaralkyl, said X having up to 20 carbons; and
m is 1 or 2.

11. A process according to claim 10 wherein A⁻ is tetrakispentafluorophenylborate.

12. A process according to claim 10 wherein the initial complex is N-tert-butylamido(tetramethyl-$\eta^5$-cyclopentadienyl)dimethylsilane titanium(III) 2-N,N-dimethylaminobenzyl and the resulting complex is N-tert-butylamido(tetramethyl-$\eta^5$-cyclopentadienyl)-dimethylsilane titanium(IV) 2-N,N-dimethylaminobenzyl tetrakispentafluorophenylborate, the initial complex is N-tert-butylamido(tetramethyl-$\eta^5$-cyclopentadienyl)-dimethylsilane titanium(IV) dibenzyl and the resulting complex is N-tert-butylamido(tetramethyl-$\eta^5$-cyclopentadienyl)dimethylsilane titanium (IV) benzyl tetrakispentafluorophenylborate, or the initial complex is N-tert-butylamido(tetramethyl-$\eta^5$-cyclopentadienyl)-dimethylsilane titanium(IV) dimethyl and the resulting complex is N-tert-butylamido(tetramethyl-$\eta^5$cyclopentadienyl)dimethylsilane titanium (IV) methyl tetrakispentafluorophenylborate.

13. An addition polymerization process comprising contacting one or more addition polymerizable monomers with a catalyst comprising a complex prepared according to any one of claims 1 to 12.

14. The process according to claim 13 wherein the addition polymerization monomers are additionally contacted with a secondary component selected from the group consisting of polymeric or oligomeric aluminoxanes and $C_{3-30}$ trialkylaluminum compounds.

15. The process according to claim 13 wherein the catalyst is supported.

16. An addition polymerization process comprising contacting one or more addition polymerizable monomers under addition polymerization conditions with a catalyst comprising the reaction product resulting from electrolyzing under inert electrolysis conditions at least one complex corresponding to the formula:

wherein:
Cp independently each occurrence is a cyclopentadienyl group $\pi$-bound to M; a hydrocarbyl, silyl, germyl, halo or halohydrocarbyl substituted derivative of said cyclopentadienyl group; or such a substituted cyclopentadienyl group wherein two such substituents together form a multiple ring structure, said Cp containing up to 50 nonhydrogen atoms, and when more than one Cp is present, different Cp moieties may be joined by a linking group, Z is a divalent moiety bound to both Cp and M(III) or M(IV) comprising boron, or a member of Group 14 of the Periodic Table of the Elements, and optionally nitrogen, phosphorus, sulfur or oxygen, said moiety having up to 30 non-hydrogen atoms, and optionally Cp and Z together form a fused ring system;

M(III) is a Group 4 metal in the +3 oxidation state;

M(IV) is a Group 4 metal in the +4 oxidation state;

X independently each occurrence is hydride; halide; or a covalently bonded ligand group selected from hydrocarbyl, silyl, germyl, and combinations thereof, said X having up to 50 carbon, silicon or germanium atoms, and oxygen, nitrogen, phosphorus or sulfur containing derivatives thereof;

a is 1 or 2;

if a is 1, b is 0 or 1, if a is 2, b is 0;

c is 1 or 2; and the sum of a+b+c equals 3.

17. A process according to claim 16 wherein M is titanium.

18. A process according to claim 16 wherein the complex that is electrolyzed corresponds to the formula:

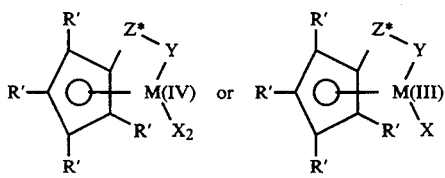

wherein:

M(IV) a Group 4 metal in the +4 oxidation state;

M(III) a Group 4 metal in the +3 oxidation state,

R' each occurrence is independently selected from the group consisting of hydrogen, alkyl, aryl, silyl, germyl, halo and combinations thereof, said R' having up to 30 non-hydrogen atoms, or two R' groups together form a divalent derivative of such groups;

Y is an anionic ligand group comprising nitrogen, phosphorus, oxygen or sulfur and having up to 20 non-hydrogen atoms, said Y being bonded to Z* and M through a chain comprising said nitrogen, phosphorus, oxygen or sulfur, and optionally Y and Z* together form a fused ring system;

Z* is SiR*$_2$CR*$_2$ SiR*$_2$SiR*$_2$, CR*$_2$CR*$_2$, CR*=CR* CR*$_2$SiR*$_2$, GeR*$_2$; wherein:

R* each occurrence is independently selected from the group consisting of hydrogen, alkyl, aryl, silyl, halogenated alkyl, halogenated aryl groups, said R* having up to 20 non-hydrogen atoms, and mixtures thereof, or two R* groups from Z*, or an R* group from Z* together with Y forms a fused ring system; and X independently each occurrence is hydride, halo, alkyl, aryl, aralkyl, allyl, hydrocarbyl substituted allyl, dialkylaminoaryl, dialkylaminoaralkyl, aryloxy or alkoxy, said X having up to 20 carbons.

19. A process according to claim 18 wherein the complex that is electrolyzed corresponds to the formula:

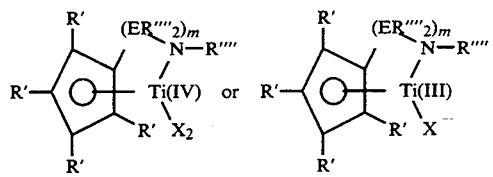

wherein:

R' each occurrence is independently selected from the group consisting of hydrogen, silyl, alkyl, aryl and combinations thereof, said R' having up to 10 carbon or silicon atoms, or two R' groups together form a divalent derivative thereof;

R'''' is C$_{1-10}$ hydrocarbyl;

E is silicon or carbon;

X is alkyl, aryl, allyl or dialkylaminoaralkyl, said X having up to 20 carbons; and m is 1 or 2.

20. A process according to claim 16 wherein the initial complex is N-tert-butylamido(tetramethyl-η5-cyclopentadienyl)dimethylsilane titanium(III) 2-N,N-dimethylaminobenzyl or N-tert-butylamido(tetramethyl-η5-cyclopentadienyl)dimethylsilane titanium(IV) dimethyl.

21. The process according to claim 16 wherein the addition polymerization monomers are additionally contacted with a secondary component selected from the group consisting of polymeric or oligomeric alumoxanes and C$_{3-30}$ trialkylaluminum compounds.

* * * * *

UNITED STATES PATENT AND TRADEMARK OFFICE
CERTIFICATE OF CORRECTION

PATENT NO. : 5,425,872
DATED : June 20, 1995
INVENTOR(S) : David D. Devore et al.

It is certified that error appears in the above-indentified patent and that said Letters Patent is hereby corrected as shown below:

Claim 7, column 11, line 49, "SIR*2" should correctly read --SiR*2--.

Claim 16, column 13, line 21, "c is 1 or 2; and" should correctly read --c is 1; and--.

Claim 18, column 14, line 3, "SIR*2CR*2" should correctly read -- SiR*2, CR*2, --

Claim 18, column 14, line 4, "CR*=CR*CR*2SiR*2" should correctly read --CR*=CR*, CR*2SiR*2, --

Signed and Sealed this

Tenth Day of December, 1996

Attest:

BRUCE LEHMAN

*Attesting Officer*    *Commissioner of Patents and Trademarks*